United States Patent [19]

Bretting

[11] Patent Number: 5,545,633
[45] Date of Patent: Aug. 13, 1996

[54] 17-ENE VITAMINE D ANALOGUES

[75] Inventor: Claus A. S. Bretting, Frederiksberg, Denmark

[73] Assignee: Leo Pharmaceutical Products Ltd. A/S (Løvens Kemiske Fabrik Produktionsaktieselskab), Ballerup, Denmark

[21] Appl. No.: 295,755

[22] PCT Filed: Jun. 7, 1993

[86] PCT No.: PCT/DK93/00196

§ 371 Date: Sep. 1, 1994

§ 102(e) Date: Sep. 1, 1994

[87] PCT Pub. No.: WO94/01398

PCT Pub. Date: Jan. 20, 1994

[30] Foreign Application Priority Data

Jul. 3, 1992 [GB] United Kingdom ............... 9214202

[51] Int. Cl.⁶ .................... A61K 31/59; C07C 401/00
[52] U.S. Cl. ....................... 514/167; 552/653; 204/166
[58] Field of Search ................. 552/653; 514/167; 204/166

[56] References Cited

FOREIGN PATENT DOCUMENTS 923414  3/1992  WIPO .

OTHER PUBLICATIONS

Chaudhuri et al: "Acid–catalysed rearrangement of 20alpha–e thynylpregn–5–ene–3beta–diol 3–acetate", Journal of the American Chemical Society, vol. 87, No. 16, Aug. 20, 1965, cited in the application.

*Primary Examiner*—Kimberly J. Prior
*Attorney, Agent, or Firm*—Cushman Darby & Cushman, LLP

[57] ABSTRACT

The invention relates to vitamin D compounds of formula (I)

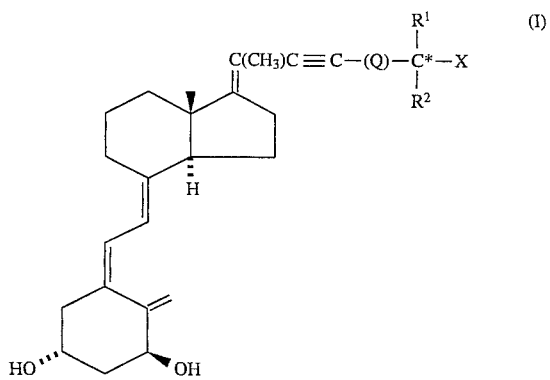

in which X is hydrogen or hydroxy; $R^1$ and $R^2$ stand for hydrogen or a $C_{1-6}$ hydrocarbyl radical which is optionally substituted with one or more deuterium or fluorine atoms, or taken together with the carbon atom bearing the group X can form a $C_{3-8}$ carbocyclic ring; Q is a single bond or a $C_{1-8}$ hydrocarbylene diradical which is optionally substituted with one or more deuterium or fluorine atoms; and derivatives of formula I. The compounds show anti-inflammatory and immunomodulating effects as well as strong activity in inducing differentiation and inhibiting undesirable proliferation of certain cells.

15 Claims, No Drawings

17-ENE VITAMINE D ANALOGUES

This application is a 371 of PCT/DK93/00196.

This invention relates to a hitherto unknown class of compounds which shows antiinflammatory and immunomodulating effects as well as strong activity in inducing differentiation and inhibiting undesirable proliferation of certain cells, including cancer cells and skin cells, to pharmaceutical preparations containing these compounds, to dosage units of such preparations, and to their use in the treatment and prophylaxis of hyperparathyroidism, particularly secondary hyperparathyroidism associated with renal failure, of a number of disease states including diabetes mellitus, hypertension, acne, alopecia, skin ageing, imbalance in the immune system, of inflammatory diseases such as rheumatoid arthritis and asthma, of diseases characterized by abnormal cell differentiation and/or cell proliferation such as e.g. psoriasis and cancer, for prevention and/or treatment of steroid induced skin atrophy, and for promoting osteogenesis and treating osteoporosis.

The compounds of the invention constitute a novel class of vitamin D analogues and are represented by the general formula I

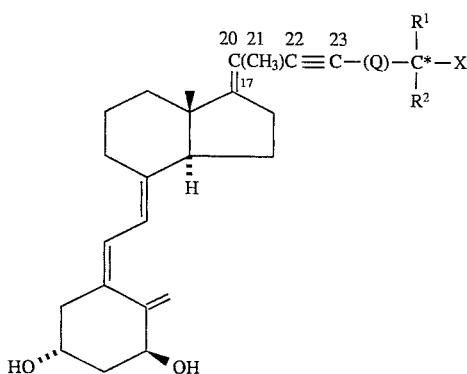

in which formula X is hydrogen or hydroxy; $R^1$ and $R^2$, which may be the same or different, stand for hydrogen or a $C_1$–$C_6$ hydrocarbyl radical; or $R^1$ and $R^2$, taken together with the carbon atom (starred in formula I) bearing the group X, can form a $C_3$–$C_8$ carbocyclic ring; Q is a single bond or a $C_1$–$C_8$ hydrocarbylene diradical. $R^1$, $R^2$, and/or Q may be optionally substituted with one or more deuterium or fluorine atoms.

In the context of this invention, the expression hydrocarbyl radical (hydrocarbylene diradical) indicates the residue after removal of 1 (2) hydrogen atom(s) from a straight, branched or cyclic saturated or unsaturated hydrocarbon.

Examples of $R^1$ and $R^2$ when taken separately include (apart from hydrogen), but are not limited to, methyl, trifluoromethyl, ethyl, vinyl, normal-, iso- and cyclo-propyl, and 1-methylvinyl.

Examples of $R^1$ and $R^2$ when taken together include di-, tri-, tetra- and penta-methylene.

Examples of Q include a single bond, methylene, di-, tri- and tetra-methylene, —$CH_2$—CH=CH—, —$CH_2$—C≡C—, —CH=CH—$CH_2$—, —C≡C—$CH_2$—, phenylene ($C_6H_4$; ortho, meta, para), —$CH_2$—($C_6H_4$)—, and —($C_6H_4$)—$CH_2$—.

The configuration about the 17, 20-double bond can be either E or Z. As can be seen from formula I, depending on the meanings of $R^1$, $R^2$, Q and X the compounds of the invention can comprise several diastereoisomeric forms (e.g. R or S configuration at the starred carbon atom). The invention covers all these diastereoisomers in pure form as well as mixtures of diastereoisomers.

In particular, both diastereoisomers having the two possible configurations about the 17, 20-double bond are included.

In addition, prodrugs of I in which one or more of the hydroxy groups are masked as groups which can be reconverted to hydroxy groups in vivo are also within the scope of the invention.

Compounds of formula I in which X is hydrogen also may act as prodrugs, as these compounds are relatively inactive in vitro, but are converted to active compounds of formula I by enzymatic hydroxylation after administration to the patient.

It has been shown that 1α,25-dihydroxy-vitamin $D_3$ (1,25(OH)$_2$D$_3$) influences the effects and/or production of interleukins (Muller, K. et al, Immunol. Lett. 17, 361–366 (1988)), indicating the potential use of this compound in the treatment of diseases characterized by a dysfunction of the immune system, e.g. autoimmune diseases, AIDS, host versus graft reactions, and rejection of transplants or other conditions characterized by an abnormal interleukin-1 production, e.g. inflammatory diseases such as rheumatoid arthritis and asthma.

It has also been shown that 1,25(OH)$_2$D$_3$ is able to stimulate the differentiation of cells and inhibit excessive cell proliferation (Abe, E. et al, Proc. Natl. Acad. Sci., U.S.A. 78, 4990–4994 (1981)), and it has been suggested that this compound might be useful in the treatment of diseases characterized by abnormal cell proliferation and/or cell differentiation such as leukemia, myelofibrosis and psoriasis.

Also, the use of 1,25(OH)$_2$D$_3$, or its pro-drug 1α-OH-D$_3$, for the treatment of hypertension (Lind, L. et al, Acta Med. Scand. 222, 423–427 (1987)) and diabetes mellitus (Inomata, S. et al, Bone Mineral, 1, 187–192 (1986)) has been suggested. Another indication for 1,25(OH)$_2$D$_3$ is suggested by the recent observation of an association between hereditary vitamin D resistance and alopecia: treatment with 1,25(OH)$_2$D$_3$ may promote hair growth (Editorial, Lancet, Mar. 4, 1989, p. 478). Also, the fact that topical application of 1,25(OH)$_2$D$_3$ reduces the size of sebaceous glands in the ears of male Syrian hamsters suggests that this compound might be useful for the treatment of acne (Malloy, V. L. et al., the Tricontinental Meeting for Investigative Dermatology, Washington, 1989).

However, the therapeutic possibilities in such indications of 1,25(OH)$_2$D$_3$ are severely limited by the well known potent effect of this hormone on calcium metabolism; elevated blood concentrations will rapidly give rise to hypercalcemia. Thus, this compound and its potent synthetic analogues are not completely satisfactory for use as drugs in the treatment of e.g. psoriasis, leukemia or immune diseases which may require continuous administration of the drug in relatively high doses.

A number of vitamin D analogues have recently been described which show some degree of selectivity in favour of the cell differentiation inducing/cell proliferation inhibiting activity as compared with the effect on calcium metabolism.

Thus, the vitamin $D_3$ analogue, calcipotriol, containing a 22,23-double bond, a 24-hydroxy group and in which the carbon atoms 25, 26 and 27 are incorporated in a three membered ring, is a potent inducer of cell differentiation and inhibitor of cell proliferation which shows only moderate activity on calcium metabolism in vivo (Binderup, L. and Bramm, E., Blochem. Pharmacol. 37, 889–895 (1988)).

However, this selectivity is not paralleled by in vitro studies, which show that calcipotriol binds equally well as 1,25(OH)$_2$D$_3$ to the intestinal vitamin D receptor. Possibly, the low in vivo activity on calcium metabolism of calcipotriol is due to a rapid metabolism of the compound, thus limiting the potential of this compound for systemic use.

24-Homo-1,25-dihydroxyvitamin D$_3$ and 26-homo-1,25-dihydroxyvitamin D$_3$ (together with their 22,23-didehydroanalogues) (Ostrem, V. K.; Tanaka, Y.; Prahl, J.; DeLuca, H. F.; and Ikekawa, N.; Proc. Natl. Acad. Sci. USA 84, 2610–14 (1987)) have been claimed to have the same binding affinity as 1,25(OH)$_2$D$_3$ to both the rat and chicken intestinal receptor and the receptor in a human myeloid leukemia cell line (HL-60), and yet to be 10-fold more potent than 1,25(OH)$_2$D$_3$ in inducing differentiation of HL-60 cells in vitro. In vivo, these compounds are respectively "significantly less potent" and "more potent" than 1,25(OH)$_2$D$_3$ in calcium metabolism assessments.

26,27-Dimethyl-1α,25-dihydroxyvitamin D$_3$ has been synthesized, but the published information regarding its biological activities is contradictory. (Sai, H.; Takatsuto, S.; Hara, N.; and Ikekawa, N.; Chem. Pharm. Bull. 33, 878–881 (1985) and Ikekawa, N.; Eguchi, T.; Hara, N.; Takatsuto, S.; Honda, A.; Mori, Y.; and Otomo, S.; Chem. Pharm. Bull. 35, 4362–4365 (1987)). The closely related 26,27-diethyl-1α,25-dihydroxyvitamin D$_3$ is also reported by these authors; in this case as having "almost no vitamin D activity" (i.e. calcium metabolism effects) while being 10-fold more potent than 1,25(OH)$_2$D$_3$ in inducing cell differentiation.

U.S. Pat. No. 4,804,502 discloses compounds containing a triple bond in the side chain of Vitamin D, and these compounds are claimed to be useful in the treatment of disease states characterized by metabolic calcium deficiencies.

The fact that there are only small structural differences between the compounds of the prior art referred to above indicates that the present state of knowledge does not allow prediction of the structure of vitamin D analogues which will show a favourable degree of selectivity, as reflected by a higher cell differentiating activity in vitro compared to the binding affinity for intestinal vitamin D receptor in vitro. Furthermore, the matter is complicated by the observation that receptor binding affinities in vitro are not always paralleled by in vivo studies, probably reflecting a pharmacokinetic difference between the compounds.

Also compounds which differ structurally from the above vitamin D analogues in the configuration of the methyl group at carbon-20 have been reported to have potent effects on cell differentiation/proliferation. This "unnatural" configuration, present in several recent patent applications including our previous international patent application number PCT/DK90/00156, filing date 19th Jun. 1990, publication number WO 91/00271, international patent application number PCT/DK91/00200, filing date 11th Jul. 1991, publication number WO 92/03414), International patent application number PCT/DK93/00105, filing date 23rd Mar. 1993, British patent application No. 9220272.0, filing date 25th Sep. 1992, British patent application No. 9220439.5, filing date 28th Sep. 1992, British patent application No. 9223061.4, filing date 4th Nov. 1992, and British patent application No. 9226877.0, filing date 23rd Dec. 1992, has surprisingly been found to have a profound and advantageous biological significance.

The compounds of the present invention differ from both C-20-epimerical types of previously known vitamin D analogues in the presence of the 17,20-double bond which gives altered stereochemical conditions. Thus, combining the advantages of both types of previously known vitamin D-analogues with the new, more fixed structure, a particular compound of formula I is observed to show one or more of the following advantages when comparison to prior art is made:

(a) more potent effects on cell differentiation/proliferation (b) a greater selectivity in favour of the potent effects on cell differentiation/proliferation contra the effects on calcium metabolism;

(c) more potent effects on the production and action of interleukins;

(d) a greater selectivity in favour of the effects on interleukin production and action versus the effects on calcium metabolism.

The compounds of the invention are therefore especially suited for both local and systemic treatment and prophylaxis of human and veterinary disorders which are characterized by 1) abnormal cell proliferation and/or cell differentiation, such as certain dermatological disorders including psoriasis and certain cancer forms, 2) an imbalance in the immune system, e.g. in autoimmune diseases, including diabetes mellitus, host versus graft reaction, and rejection of transplants; and additionally for the treatment of inflammatory diseases, such as rheumatoid arthritis and asthma. Acne, alopecia, and hypertension are other conditions which may be treated with the compounds of the invention. Finally, as thickening of the skin is observed after topical treatment with the compounds of the invention, these compounds may be useful for treatment or prevention of skin ageing, including photo-ageing.

Because of the low tendency of the compounds to produce hypercalcemia on continued administration they are expected to be valuable for the long term treatment of hyperparathyroidism (particularly secondary hyperparathyroidism associated with renal failure) and for promoting osteogenesis and treating osteoporosis. For these indications the presently described compounds have a higher therapeutic ratio than the prior art compounds (see U.S. Pat No. 4,948,789 and EP 0385446 A2).

The present compounds may be used in combination with other pharmaceuticals. In the prevention of graft rejection and graft versus host reaction, a treatment with the present compounds may advantageously be combined with e.g. a cyclosporin treatment.

Compounds I can be prepared from the vitamin D-derived ketone compound 1 (Scheme 1), a synthesis of which has been reported [Hansen K., Calverley M. J. and Binderup L.: Synthesis and Biological Activity of 22-Oxa Vitamin D analogues. In: Vitamin D, Proc. Eighth Workshop on Vitamin D, Paris, Jul. 5–10, 1991, p. 161; Walter de Gruyter, Berlin 1991], for example by the routes outlined in Scheme 1.

The following standard abbreviations are used throughout this disclosure: Me=methyl; Et=ethyl; Bu=n-butyl; THP=tetrahydro-4H-pyran-2-yl; TMS=trimethylsilyl; DMAP=4-dimethylaminopyridine; pet. ether=petroleum ether; THF=tetrahydrofuran; TBAF=tetra-(n-butyl)-ammonium fluoride; b.p.=boiling point; PLC=preparative thin-layer chromatography; Tf=trifluoromethane sulfonyl; DMF=N,N-dimethylformamide; "HF"=5% hydrogen fluoride in acetonitrile:water (7:1); TBDMS=tert-butyldimethylsilyl; HCl=hydrochloric acid; "NaHCO$_3$"=saturated aqueous sodium bicarbonate solution; A$^1$A$^2$A$^3$SiZ: a silylating agent where A$^1$, A$^2$ and A$^3$, which may be the same or different stand for C$_1$–C$_6$ hydrocarbyl, C$_1$–C$_6$ hydrocarbyloxy, or aryl, and Z stands for a good leaving group, such as -Cl, -Br or -OTf (trifluoromethane sulfonate or triflate); NOE=nuclear Overhauser enhancement; PPTS=pyridinium-p-toluensulfonate.

Scheme 1
Synthesis of Compounds I of the Invention
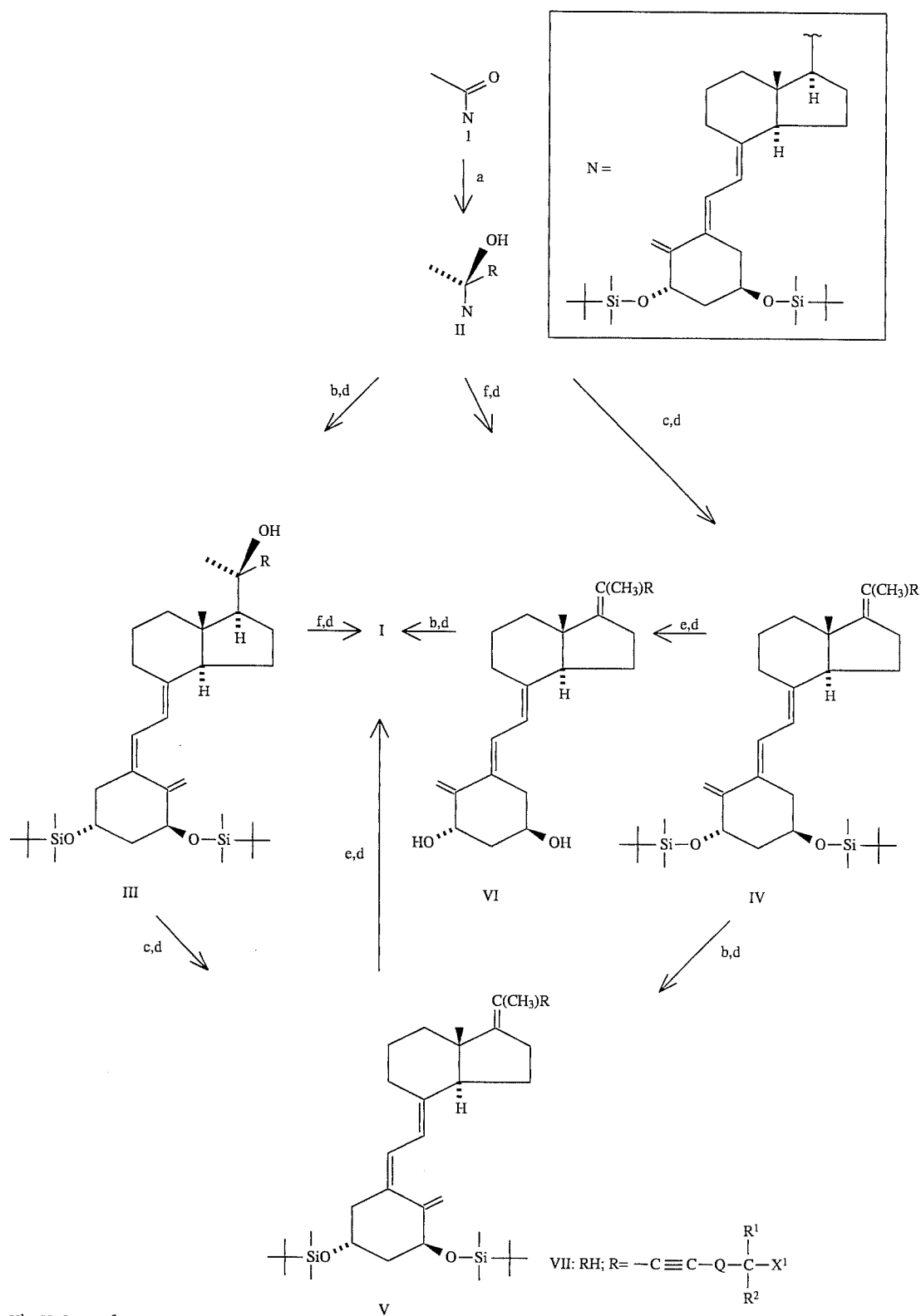
$X^1$ = H, OH, OR$^3$
$R^3$ = alcohol protective group, e.g. $A^1A^2A^3$Si or THP
$R^1$, $R^2$, Q, $A^1$, $A^2$ and $A^3$ have the above meanings.
Notes to Scheme 1

-continued
Scheme 1
Synthesis of Compounds I of the Invention a) (i) Compound 1 is reacted with the anion R⁻, derived from the side chain building block, RH, of general formula VII, with a suitable base.
(ii) The major product, the (presumed) R-compound of the two possible C-20 epimers, is isolated by chromatography.
b) Isomerization of compounds II, IV or VI to the corresponding compound III, V or I, by means of UV-light in the presence of a triplet sensitizer, e.g. anthracene.
c) (i) Dehydration of compounds II or III to the corresponding compound IV or V by treatment with an anhydrous acid under suitable conditions, e.g. with phosporic acid (0.2 M, in acetonitrile at 50° C. for 1–2 hours. Acid-sensitive protective groups, such as THP, may be removed during this step, too.
(ii) If both 17, 20-ene isomers are formed, they may be separated here, or alternatively this may be done at a later stage. Separation and purification are preferably accomplished by chromatography.
d) Optional functional group modification in the side chain.
e) Deprotection of Compound IV or V to compound VI or I, respectively, e.g. by means of "HF " or TBAF.
f) Dehydration, accompanied by deprotection, of Compounds II or III to Compound VI or I, respectively, e.g. by means of "HF".

Notes to Scheme 1 a)
(i) Compound 1 is reacted with the anion R⁻, derived from the side chain building block, RH, of general formula VII, with a suitable base.
(ii) The major product, the (presumed) R-compound of the two possible C-20 epimers, is isolated by chromatography.

b)
Isomerization of compounds II, IV or VI to the corresponding compound III, V or I, by means of UV-light in the presence of a triplet sensitizer, e.g. anthracene.

c)
(i) Dehydration of compounds II or III to the corresponding compound IV or V by treatment with an anhydrous acid under suitable conditions, e.g. with phosphoric acid (0.2M, in acetonitrile at 50° C. for 1–2 hours. Acid-sensitive protective groups, such as THP, may be removed during this step, too.
(ii) If both 17,20-ene isomers are formed, they may be separated here, or alternatively this may be done at a later stage. Separation and purification are preferably accomplished by chromatography.

d)
Optional functional group modification in the side chain.

e)
Deprotection of Compound IV or V to compound VI or I, respectively, e.g. by means of "HF" or TBAF.

f)
Dehydration, accompanied by deprotection, of Compounds II or III to Compound VI or I, respectively, e.g. by means of "HF".

The side chain building blocks RH of general formula VII are either known compounds, or they can be prepared by standard methods known to the specialist. In particular, this applies to the side chain building blocks necessary for the preparation of the exemplified compounds (101–147). In the cases where no specific indications are given, the procedures according to Scheme 1 can be carried out analogously to the specific preparations and examples mentioned in the following.

As a nonlimiting illustration, the preparation of some compounds of the general formula VII where $Q=(CH_2)_n$, (n=0–3), $X^1=OR^3$ and $R^3=-SiA^1A^2A^3$ or THP is outlined in Scheme 2, but similar compounds of formula VII with other Q and/or $X^1$ may be prepared by analogous methods. Some specific side chain building blocks RH are listed in Table 1 and their syntheses are described in the preparations.

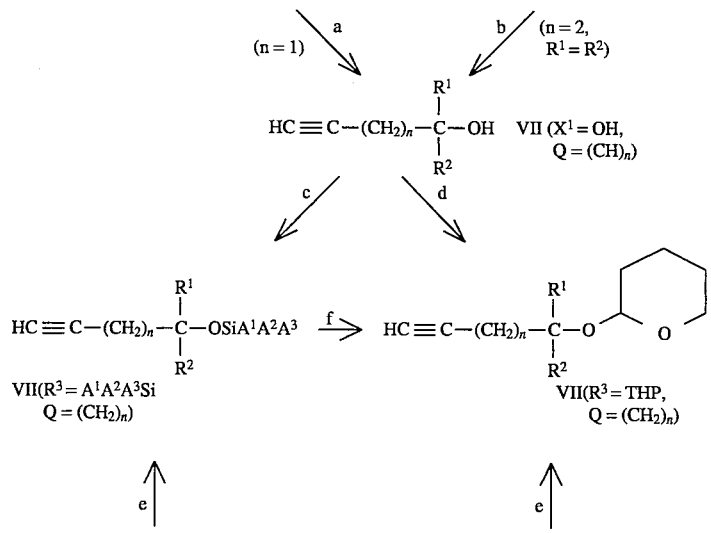

-continued
Scheme 2
Synthesis of some Side Chain Building Blocks VII

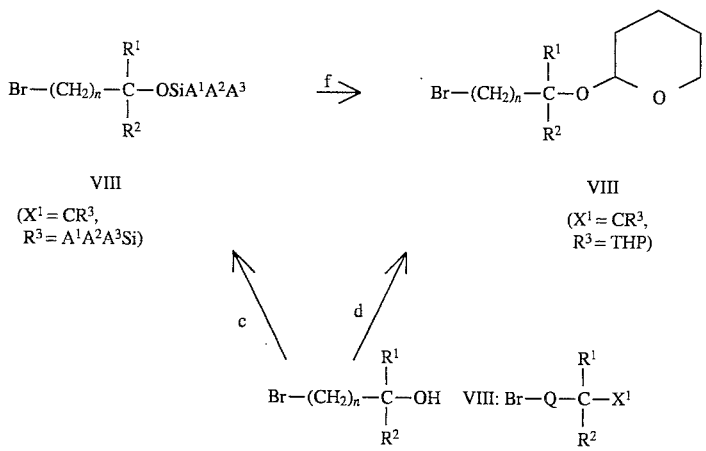

VIII ($X^1 = $ OH)   $X^1 = $ H, OH, $OR^3$, Q = $(CH_2)_n$

Notes to Scheme 2
a. (i) Al,
(ii) $R^1R^2C=O$;
b. Grignard reagent $R^1$MgBr or $R^1$MgI;
c. $A^1A^2A^3$SiZ/base;
d. dihydropyran/acid;
e. acetylene/Na/liq.$NH_3$;
f. ($A^1A^2A^3 = Me_3$)
(i) MeOH/acid,
(ii) dihydropyran/acid.

TABLE 1

Some Side Chain Building Blocks, RH of General Formula VII
(Q = $(CH_2)_n$, n = 0-3, $R^1 = R^2 = CH_3$ or $C_2H_5$; $R^3$ = TMS,
TBDMS or THP)

| Prep. Number | Compound Number | General Procedure | RH |
|---|---|---|---|
| 16 | 18 | 4 | H—≡—⟨—OSi⟨ |
| 17 | 19 | 2 | H—≡—⟨—O⟨O⟩ |
| 2 | 3 | 2 | H—≡—⟨—O⟨O⟩ (Et) |
| 19 | 21 | 2 | H—≡—⟨⟨—O⟨O⟩ |
| 4 | 5 | 4 | H—≡—⟨⟨—O—TBDMS |

TABLE 1-continued

Some Side Chain Building Blocks, RH of General Formula VII
($Q = (CH_2)_n$, n = 0-3, $R^1 = R^2 = CH_3$ or $C_2H_5$; $R^3$ = TMS, TBDMS or THP)

| Prep. Number | Compound Number | General Procedure | RH |
|---|---|---|---|
| 6 | 7 | 6 | H—≡—⋀—⋁—C(—O—tetrahydropyranyl) |

Intermediates for the preparation of the side chain building blocks, RH of Table 1, are either known compounds or can e.g. be prepared from the compounds listed in Table 2. The syntheses of these compounds are described in the Preparations.

TABLE 2

Some Intermediates for the Synthesis of the RH (VII) of Table 1

| Type | Prep. No. | Compound No. | General Procedure | Formula |
|---|---|---|---|---|
| VII | 1 | 2 | 1 | H—≡—⋀—C(—OH) |
| VII | 18 | 20 | 3 | H—≡—⋀—C(—OH) |
| VII | 3 | 4 | 3 | H—≡—⋀—C(—OH) |
| VIII | 5 | 6 | 5 | Br—⋀—⋁—C(—O—tetrahydropyranyl) |

The reaction of the ketone, compound 1, with the side chain building blocks, RH=H—C≡C—Q—$C(R^1)(R^2)X^1$, can be performed by standard methods of nucleophilic addition of acetylenic anions ($R^-$) to carbonyl compounds; i.e. by treating the RH with a suitable base, such as n-BuLi, in a suitable anhydrous solvent, such as THF, then adding 1, to give II after usual aqueous work-up (which is normally implied in all the reactions of Schemes I and II).

In general the reaction product II is a mixture of the two possible C-20-epimers. It is usually preferable to separate these epimers which can conveniently be done by chromatography.

One epimer is formed in much higher yield than the other and is usually less polar chromatographically. This major epimer is by analogy with similar reactions assumed to be the 20-R-form, and it is this epimer which is used in the reactions shown in Scheme 1, leading to compounds I of the invention. Table 3 contains non-limiting illustrations of such compounds of formula II, and furthermore other such intermediates of the types III, IV and V of Scheme 1 are listed in Table 3, too.

The dehydration of Compound II or III in which a C-20 OH group is eliminated together with the C-17 H is preferably performed by a rather mild acidic elimination which conveniently can be achieved by treatment with anhydrous phosphoric acid in acetonitrile as described in General Procedure 9.

Alternatively, it is possible to perform the 17,20-dehydration of compound II or III simultaneously with the removal of sufficiently labile protective groups, by treatment with "HF" as described in General Procedure 10.

Both procedures are illustrated in Scheme 1.

By the dehydration leading to compounds containing a 17,20 double bond it is possible to get two different isomers: the E- and the Z-form. Usually, one form is formed as the predominant one, and is, after purification, used as intermediate, leading ultimately to compound I. This is the case of compounds 13, 15 and 17. Occasionally, as in the case of isomeric compounds 13 and 14, it is possible to isolate the other, minor, 17,20-ene isomer as well. By comparing the $^1$H-NMR chemical shifts of the 21-methyl groups of compound 13 (δ 1.72) and of compound 14 (δ 1.84) with values described in the literature for steroids with a similar 17,20-ene, 22,23-yne structure (Chaudhuri, N. K., et al, JACS 87, 3737 (1965)) it seems likely that compound 13 is the Z-form and compound 14 is the E-form, so it is reasonable to assume that the other (major) isomers, compounds 15 and 17, are the Z-forms as well. Furthermore, compound 14 shows an NOE effect between H 18 and H 21 and also between H 18 and an equatorial H 12, as would be expected for the E-configuration, and compound 13 shows NOE between H 16 and H 21 consistent with the Z-form. Although somewhat tentatively, the following compounds are consequently listed as the Z-forms: Compounds 13, 15, 16, 17, 101, 102 and 103. Listed as E-forms are: Compounds 14, 22 and 112.

Exemplified Compounds I of the invention are listed in Table 4, the numbered examples giving reference to illustrative methods of synthesis, together with spectroscopic data for those same compounds of the examples.

It should be noted that the preparations and examples of Schemes 1 and 2 are illustrative only, as the particular synthesis of each step and the order in which each step is performed can be varied greatly. Furthermore, the radical R: —C≡C—Q—C($R^1$)($R^2$)($X^1$) may optionally be as specified or be a radical which can be converted to the said radical at any convenient later stage (or over several stages). Thus R in compounds II, III, IV, V, VI and I does not necessarily have the same meaning along a particular synthetic sequence. The conversion of R to —C≡C—Q—C($R^1$)($R^2$)$X^1$ may well involve several steps and possibly involve a temporary protection of the sensitive triene system of the molecule. Apart from any necessary modification within the side chain (R), the conversion of II to I involves a photoisomerisation step and a deprotection step (if not performed already, simultaneously with the 17,20-dehydration step as mentioned above), analogous to the steps used in the last stages of the synthesis of other vitamin D analogues (see European patent No. 0 227 836).

TABLE 3

Intermediates of formulas II, III, IV and V; $Q = (CH_2)_n$

| Type (See Scheme 1) | Preparation No. | Compound No. | General Procedure | Δ17,20 E/Z | $R^1 = R^2$ | n | $X^1$ |
|---|---|---|---|---|---|---|---|
| II | 7 | 8 | 7 | — | Et | 1 | OTHP |
| II | 8 | 9 | 7 | — | Et | 2 | OTBDMS |
| II | 9 | 10 | 7 | — | Et | 3 | OTHP |
| III | 10 | 11 | 8 | — | Et | 1 | OTHP |
| III | 11 | 12 | 8 | — | Et | 3 | OTHP |
| IV | 12 | 13 | 9 | Z | Et | 2 | OTBDMS |
| IV | 12 | 14 | 9 | E | Et | 2 | OTBDMS |
| V | 13 | 15 | 9 | Z | Et | 1 | OH |
| V | 14 | 16 | 8 | Z | Et | 2 | OTBDMS |
| V | 15 | 17 | 9 | Z | Et | 3 | OH |
| V | 20 | 22 | 8 | E | Et | 2 | OTBDMS |

TABLE 4

Exemplified Compounds of General Formula I

| Example No. | Compound No. | General Procedure | Δ17,20 E/Z | $R^1$ | $R^2$ | X | n[1] | $Q^{2)}$ |
|---|---|---|---|---|---|---|---|---|
| 1 | 101 | 10 | Z | Et | Et | OH | 1 | |
| 2 | 101 | 11 | Z | Et | Et | OH | 1 | |
| 3 | 102 | 10 | Z | Et | Et | OH | 2 | |
| 4 | 102 | 11 | Z | Et | Et | OH | 2 | |
| 5 | 103 | 11 | Z | Et | Et | OH | 3 | |
| | 104 | 10 or 11 | E | Et | Et | OH | 0 | |
| | 105 | 10 or 11 | Z | Et | Et | OH | 0 | |
| | 106 | 10 or 11 | E | Me | Me | OH | 1 | |
| | 107 | 10 or 11 | Z | Me | Me | OH | 1 | |
| | 108 | 10 or 11 | E | Et | Et | OH | 1 | |
| | 109 | 10 or 11 | Z | $CF_3$ | $CF_3$ | OH | 1 | |
| | 110 | 10 or 11 | E | Me | Me | OH | 2 | |
| | 111 | 10 or 11 | Z | Me | Me | OH | 2 | |
| 6 | 112 | 11 | E | Et | Et | OH | 2 | |
| | 113+ | 10 or 11 | Z | Me | Et | OH | 2 | |
| | 114++ | 10 or 11 | Z | Me | Et | OH | 2 | |
| | 115 | 10 or 11 | E | $CF_3$ | $CF_3$ | OH | 2 | |
| | 116 | 10 or 11 | Z | $CF_3$ | $CF_3$ | OH | 2 | |
| | 117 | 10 or 11 | E | Et | Et | H | 2 | |
| | 118 | 10 or 11 | Z | Et | Et | H | 2 | |
| | 119 | 10 or 11 | Z | Me | Me | OH | | CH=CH, Δ24,25E |
| | 120 | 10 or 11 | Z | Et | Et | OH | | CH=CH, Δ24,25E |
| | 121 | 10 or 11 | Z | Me | Me | OH | | CH=CH, Δ24,25Z |
| | 122 | 10 or 11 | Z | Et | Et | OH | | CH=CH, Δ24,25Z |
| | 123 | 10 or 11 | E | Me | Me | OH | 3 | |
| | 124 | 10 or 11 | Z | Me | Me | OH | 3 | |

TABLE 4-continued

Exemplified Compounds of General Formula I

| Example No. | Compound No. | General Procedure | Δ17,20 E/Z | $R^1$ | $R^2$ | X | $n^{1)}$ | $Q^{2)}$ |
|---|---|---|---|---|---|---|---|---|
| | 125 | 10 or 11 | E | Et | Et | OH | 3 | |
| | 126+ | 10 or 11 | Z | Me | Et | OH | 3 | |
| | 127++ | 10 or 11 | Z | Me | Et | OH | 3 | |
| | 128 | 10 or 11 | E | $CF_3$ | $CF_3$ | OH | 3 | |
| | 129 | 10 or 11 | Z | $CF_3$ | $CF_3$ | OH | 3 | |
| | 130 | 10 or 11 | E | Et | Et | H | 3 | |
| | 131 | 10 or 11 | Z | Et | Et | H | 3 | |
| | 132 | 10 or 11 | Z | Me | Me | OH | | —CH=CH—$CH_2$—,Δ24,25E |
| | 133 | 10 or 11 | E | Et | Et | OH | | —CH=CH—$CH_2$—,Δ24,25E |
| | 134 | 10 or 11 | Z | Et | Et | OH | | —CH=CH—$CH_2$—,Δ24,25E |
| | 135 | 10 or 11 | Z | Me | Me | OH | | —CH=CH—$CH_2$—,Δ24,25Z |
| | 136 | 10 or 11 | E | Et | Et | OH | | —CH=CH—$CH_2$—,Δ24,25Z |
| | 137 | 10 or 11 | Z | Et | Et | OH | | —CH=CH—$CH_2$—,Δ24,25Z |
| | 138 | 10 or 11 | E | Et | Et | OH | | —$CH_2$—CH=CH—,Δ25,26E |
| | 139 | 10 or 11 | Z | Et | Et | OH | | —$CH_2$—CH=CH—,Δ25,26E |
| | 140 | 10 or 11 | E | Et | Et | OH | | —$CH_2$—CH=CH—,Δ25,26Z |
| | 141 | 10 or 11 | Z | Et | Et | OH | | —$CH_2$—CH=CH—,Δ25,26Z |
| | 142 | 10 or 11 | E | Me | Me | OH | | m-$C_6H_4$ |
| | 143 | 10 or 11 | Z | Me | Me | OH | | m-$C_6H_4$ |
| | 144 | 10 or 11 | E | Et | Et | OH | | m-$C_6H_4$ |
| | 145 | 10 or 11 | Z | Et | Et | OH | | m-$C_6H_4$ |
| | 146 | 10 or 11 | E | Et | Et | OH | 4 | |
| | 147 | 10 or 11 | Z | Et | Et | OH | 4 | |

$^{1)}$If Q = $(CH_2)_n$
$^{2)}$If Q ≠ $(CH_2)_n$
+(R) configuration at starred carbon atom
++(S) configuration at starred carbon atom The present compounds are intended for use in pharmaceutical compositions which are useful in the treatment of human and veterinary disorders as described above.

The amount required of a compound of formula I (hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders. In the treatment of dermatological disorders like psoriasis or eye diseases topical or enteral forms are preferred.

In the treatment of respiratory diseases like asthma an aerosol is preferred.

While it is possible for an active ingredient to be administered alone as the raw chemical, it is preferable to present it as a pharmaceutical formulation. Conveniently, the active ingredient comprises from 0.1 ppm to 0.1% by weight of the formulation.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include e.g. those in a form suitable for oral, rectal, parenteral (including subcutaneous, intramuscular and lntravenous), intra-articular and topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed by a binder, lubricant, inert diluent, surface active or dispersing agent. Moulded tablets may be made by moulding, in a suitable machine, a mixture of the powdered active ingredient and suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops.

For asthma treatment inhalation of powder, self-propelling or spray formulations, dispensed with a spray can, a nebulizer or an atomizer can be used. The formulations, when dispensed, preferably have a particle size in the range of 10 to 100μ.

Such formulations are most preferably in the form of a finely comminuted powder for pulmonary administration from a powder inhalation device or self-propelling powder-dispensing formulations. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. The liquid propellant may be any propellant known to be suitable for medicinal administration and may comprise one or more $C_1$–$C_6$-alkyl hydrocarbons or halogenated $C_1$–$C_6$-alkyl hydrocarbons or mixtures thereof; chlorinated and fluorinated $C_1$–$C_6$-alkyl hydrocarbons are especially preferred. Generally, the propellant constitutes 45 to 99.9% w/w of the formulation whilst the active ingredient constitutes 0.1 ppm to 0.1% w/w, of the formulation.

In addition to the aforementioned ingredients, the formulations of this invention may include one or more additional ingredients such as diluents, buffers, flavouring agents, binders, surface active agents, thickeners, lubricants, preservatives, e.g. methyl hydroxybenzoate (including antioxidants), emulsifying agents and the like.

The compositions may further contain other therapeutically active compounds usually applied in the treatment of the above mentioned pathological conditions.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the treatment of systemic disorders daily doses of from 0.1–100 μg, preferably from 0.2–25 μg, of a compound of formula I are administered. In the topical treatment of dermatological disorders, ointments, creams or lotions containing from 0.1–500 μg/g, and preferably from 0.1–100 μg/g, of a compound of formula I are administered. For topical use in ophthalmology ointments, drops or gels containing from 0.1–500 μg/g, and preferably from 0.1–100 μg/g, of a compound of formula I are administered. The oral compositions are formulated, preferably as tablets, capsules, or drops, containing from 0.05–50 μg, preferably from 0.1–25 μg, of a compound of formula I, per dosage unit.

The invention will now be further described in the following non-limiting General Procedures, Preparations and Examples:

GENERAL PROCEDURES, PREPARATIONS AND EXAMPLES

General

The exemplified compounds I are listed in Table 4.

For nuclear magnetic resonance spectra (300 Mhz) chemical shift values (δ) are quoted for deuteriochloroform solutions relative to internal tetramethylsilane (δ=0) or chloroform (δ=7.25). The value for a multipier, either defined (doublet (d), triplet (t), quartet (q)) or not (m) at the approximate mid point is given unless a range is quoted (s=singlet, b=broad). Coupling constants (J) are given in Hertz, and are sometimes approximated to the nearest unit.

Ether is diethyl ether, and was dried over sodium. THF was dried over sodium-benzophenone. Petroleum ether refers to the pentane fraction. Reactions were run at room temperature unless otherwise noted. The work-up procedure referred to involves dilution with the specified solvent (otherwise the organic reaction solvent), extraction with water and then brine, drying over anhydrous $MgSO_4$, and concentration in vacuo to give a residue. Chromatography was performed on silica gel.

General Procedures

General Procedure 1:

Reaction of ketones $R^1R^2C=O$ with organometallic reagent prepared from propargylbromide and aluminium to give the corresponding tertiary alcohol VII (Scheme 2, Table 2) (Preparation 1)

A mixture of aluminium scales (3.6 g), mercuric chloride (0.1 g) and dry THF (20 ml) was stirred at 20° C. for 20 minutes, under argon. A solution of propargyl bromide (23.8 g) in dry THF (20 ml) was added with stirring during 40 minutes, keeping the temperature at 25°–30° C. by intermittent cooling. The reaction mixture was stirred at 40°–45° C., heating as necessary, for 30 minutes. After cooling to about 25° C., a solution of the appropriate ketone, $R^1R^2C=O$ (0.2 mol) in dry ether (25 ml) was added during one hour, with stirring, cooling slightly to keep the temperature at about 25° C. Stirring was continued for a further half hour at 30°–35° C., after which the reaction mixture was worked up (ether). The residue was purified by distillation in vacuo through a 50 cm Podbielniak column to yield the title compound of the preparation as an oil.

General Procedure 2:

Protection of tertiary alcohols VII or VIII to give the corresponding 2-tetrahydropyranyl compounds VII or VIII (SCheme 2, Table 1) (Preparations 2, 17, and 19)

A mixture of the appropriate compound VII or VIII (0.01 mol), 3,4-dihydro-2H-pyran (1.26 g), PPTS (0.25 g) and dry dichloromethane (25 ml) was stirred under argon for 4 hours at 20° C. To the reaction mixture was added 100 ml of ether and 50 ml of semi-saturated aqueous sodium chloride solution. The organic phase was separated, dried and evaporated in vacuo to yield a crude product which was purified by chromatography (mixture of ether and pet. ether as eluant) to yield the title compound of the preparation.

General Procedure 3:

Reaction of 4-pentinoic acid ethyl[1] ester with Grignard reaagents, $R^1MgX^2$, to give the corresponding tertiary alcohol VII (Scheme 2, Table 2) (Preparations 3 and 18) ($X^2$=Cl, Br, I)

To 1.1 g magnesium turnings (Grignard quality) in a dry flask, was added dropwise with stirring a solution of the appropriate alkyl halogenide $R^1X^2$ (0.045 mol) in dry ether (20 ml). The reaction took place under argon, with stirring, and with reflux, and lasted 20 minutes. Stirring and reflux was continued for a further 10 minutes.

This Grignard reagent was transferred to an addition funnel, under argon, and added dropwise with stirring and cooling to about −20° C., to a solution of 4-pentinoic acid ethyl[1] ester (1.9 g) in dry ether (20 ml). The addition lasted 15 minutes, and after that stirring was continued for 20 minutes at −20° C. and for one hour at 30° C.

[1] an equimolar amount of a corresponding other lower alkyl ester, e.g. the methyl or propyl ester may be used instead of the ethyl ester.

The reaction mixture was poured into a mixture of 100 g ice/water and 4N hydrochloric acid (15 ml) under stirring. After addition of aqueous sodium bicarbonate solution to render a pH of circa 5, the mixture was extracted twice with ether (25 ml each). The combined organic phases were washed with water and saturated aqueous sodium chloride solution, dried and evaporated in vacuo to yield a crude product. This was purified either by distillation in vacuo or by chromatography (mixture of ether and pet. ether as eluant) to yield the title compound of the preparation.

General Procedure 4:

Protection of tertiary alcohols VII or VIII to give the corresponding $A^1A^2A^3$ silyl compound VII or VIII (Scheme 2. Table 1) (Preparations 4 and 16)

To solution of the appropriate compound VII or VIII (14 mM) in a suitable dry solvent, e.g. dichloromethane or DMF, was added one or more suitable base(s), e.g. triethylamine, DMAP or imidazole, under argon and with stirring and cooling in an ice bath. A suitable silylating agent, $A^1A^2A^3SiZ$, e.g. TMSCl, TBDMSOTf, triethylsilyltriflate or diphenylmethylsilyl chloride, was added dropwise with stirring during 20 minutes at 0° C. Stirring was continued for a sufficient time (typically for 0.5 to 24 hours) at a suitable temperature (typically 25° C. to 50° C.). After a suitable work-up the crude product was purified by chromatography to yield the title compound of the preparation.

General Procedure 5:

Conversion of TMS-protected alcohols of type VII or VIII to the corresponding THP-protected compound of type VII or VIII (Scheme 2, Table 2) (Preparation 5)

To a solution of the appropriate TMS-protected tertiary alcohol VII or VIII (0.02 mol) in methanol (25 ml) was added 5 drops of 6M hydrogen chloride in methanol and the mixture was stirred for 15 minutes at 20° C. The reaction mixture was evaporated until the methanol was removed, and the residue was redissolved in dichloromethane (40 ml). To this solution was added 3,4-dihydro-2-H-pyran (3.3 g) and PPTS (0.16 g) in portions under stirring and cooling in an ice-bath. After that, the mixture was stirred at 20° C. for three hours and then diluted with ether (200 ml). The ether phase was extracted with saturated aqueous sodium bicarbonate, water and saturated aqueous sodium chloride, dried and evaporated in vacuo to yield a crude product. This was purified by chromatography (mixture of ether and pet. ether as eluant) to yield the title compound of the preparation as an oil.

General Procedure 6:

Conversion of compounds VIII, with a terminal bromine atom, to the corresponding compound VII, with a terminal ethynyl group (Scheme 2, Table 1) (preparation 6)

Through dry liquid ammonia (circa 75 ml) dry acetylene was bubbled at a rate of about 200 ml per minute with stirring. At the same time sodium (0.5 g) was added in small pieces during 5 minutes. After about 5 minutes more, the flow of acetylene was discontinued, and the appropriate bromo-compound VIII (3 mmol) was added during 5 minutes; stirring at room temperature was continued until all of the ammonia had evaporated (2 to 4 hours). Pet. ether (100 ml) and ice/water (100 g) was added under stirring. The organic phase was separated, washed several times with water until neutral, dried and evaporated in vacuo to yield a crude product. This was purified by chromatography (dichloromethane or mixture of dichloromethane and pet. ether as eluants) to yield the title compound of the preparation.

General Procedure 7:

Reaction of Compound 1 with side chain building blocks VII (RH) to yield Compound II (Scheme 1, Table 3) (Preparations 7–9)

To a solution of the appropriate compound VII (1.5 mmol) in dry THF (5 ml), cooled to −70° C. and stirred under argon, was added dropwise, during 2 minutes, a solution of n-butyllithium (1.6 mM in hexane; 0.65 ml). Stirring was continued at −70° C. for 10 minutes and then at 20° C. for one hour. The mixture was again cooled to 31 70° C., and a solution of the ketone, compound 1 (0.28 g; 0.5 mmole) in dry THF (5 ml) was added dropwise, during 4 minutes, and after that, stirring was continued at −70° C. for 30 minutes. The reaction mixture was worked up (ether) to yield a crude product which was purified by means of chromatography (mixture of ether and pet. ether as eluant) to yield the title compound of the preparation.

General Procedure 8:

Isomerization of Compounds II, IV or VI to the corresponding compound III, V or I (Scheme 1, Table 3) (Preparations 10, 11 and 14)

A solution of the appropriate compound II, IV or VI (0.3 mmol), anthracene (100 mg) and triethylamine (0.05 ml) in dichloromethane (20 ml) under argon in a Pyrex flask was irradiated with UV-light from a high pressure ultraviolet lamp, type TQ760Z2 (Hanau) at about 10° C. for 20 minutes under stirring. The reaction mixture was concentrated in vacuo and treated with pet. ether (2×5 ml). After filtering the filtrate was concentrated in vacuo and purified by chromatography (mixture of ether and pet. ether as eluant) to yield the title compound of the preparation or example.

General Procedure 9:

Dehydration of tertiary alcohols II or III by phosphoric acid in acetonitrile to give the corresponding 17,20-ene compounds IV or V (Scheme 1, Table 3) (Preparations 12–13 and 15)

To a solution of the appropriate compound II or III (1 mmol) in a 1:1 mixture of acetonitrile and ethyl acetate (25 ml) was added a 0.2M solution of anhydrous phosphoric acid in acetonitrile (10 ml) under argon and with stirring at 50° C. Stirring was continued for one hour at 50° C. The reaction mixture was worked up (ethyl acetate with an additional extraction with "NaHCO₃"). The residue was purified by chromatography with a suitable eluant, if necessary by repeated chromatography, conveniently on a Waters Prep-500® machine or by PLC.

General Procedure 10

Deprotection of Compounds IV or V or, alternatively, dehydration, accompanied by deprotection, of Compounds II or III, to the corresponding Compound VI or I by treatment with "HF" (Scheme 1, Table 4) (Examples 1 and 3)

To a solution of the appropriate compound II, III, IV or V (0.07 mmol) in ethyl acetate (0.2 ml) was added acetonitrile (2 ml) followed by a 5% solution of hydrofluoric acid in acetonitrile:water, 7:1 (1.2 ml) under argon and with stirring. Stirring was continued for 10–60 minutes at 20° C. to 60° C. Saturated aqueous sodium bicarbonate solution (10 ml) was added, and the reaction mixture was worked up (ethyl acetate) The residue was purified by chromatography (ethyl acetate or a mixture of ethyl acetate and hexane or pentane as eluant) to yield the title compound of the preparation or example.

General Procedure 11:

Deprotection of Compounds IV or V to the corresponding Compound VI or I by treatment with TBAF (Scheme 1, Table 4) (Examples 2, 4, 5 and 6)

To a solution of the appropriate compound IV or V (0.07 mmol) in THF (6 ml) was added TBAF (120 mg) dissolved in THF (4 ml) under argon and with stirring. Stirring was continued for 1–30 hours at 60°–150° C. (in a closed pressure-proof vessel, if needed). Saturated aqueous sodium bicarbonate solution (10 ml) was added, and the reaction mixture was worked up (ethyl acetate) The residue was purified by chromatography (ethyl acetate or a mixture of ethyl acetate and hexane or pentane as eluant) to yield the title compound of the preparation or example.

Preparation 1: Compound 2

Method: General Procedure 1.
Starting material: Diethyl ketone.
B.p. of Compound 2: 71°–72° C./30 mbar.
NMR: $\delta$=0.90 (t, 6H), 1.60 (m, 4H), 1.75 (s, 1H), 2.05 (t, 1H), 2.35 (m, 2H).

Preparation 2: Compound 3

Method: General Procedure 2.
Starting material VII: Compound 2.
Chromatography eluant: 0% to 5% ether in pet. ether.
NMR: $\delta$=0.90 (m, 6H), 1.45–1.92 (m, 10H), 1.96 (t, 1H), 2.46 (d, 2H.), 3.47 (m, 1H), 3.98 (m, 1H), 4.81 (m, 1H).

Preparation 3: Compound 4

Method: General Procedure 3.
Starting material: Ethyl magnesium bromide.
Chromatography eluant: 25% ether in pet. ether.
NMR: $\delta$=0.87 (t, 6H), 1.48 (m, 4H), 1.71 (m, 2H), 1.97 (t, 2H), 2.26 (m, 2H).

Preparation 4: Compound 5

Method: General Procedure 4.
Starting material VII: Compound 4.
Solvent: Dichloromethane (30 ml).
Base: 2,6 lutidine (6.8 ml).
Silylating agent: TBDMSOTf (9.6 ml).
Reaction temperature: 25° C.
Reaction time: 0.5 hour.

Work-up: Ether, with additional extractions with 1N HCl followed by "NaHCO$_3$".
Chromatography eluant: 0% to 10% ether in pet. ether.
NMR: $\delta$=0.07 (s, 6H), 0.83 (t, 6H), 0.87 (s, 9H), 1.46 (m, 4H), 1.70 (m, 2H), 1.91 (t, 1H), 2.19 (m, 2H).

Preparation 5: Compound 6

Method: General Procedure 5.
Starting material VIII: 1-Bromo-4-ethyl-4-trimethylsilyloxyhexane.
Chromatography eluant: 10% ether in pet. ether.
NMR: $\delta$=0.83 (m, 6H), 1.45–2.05 (m, 14H), 3.43 (t, 2H), 3.45 (m, 1H), 3.94 (m, 1H), 4.68 (m, 1H).

Preparation 6: Compound 7

Method: General Procedure 6.
Starting material VIII: Compound 6.
Chromatography eluant: Dichloromethane.
NMR: $\delta$=0.83 (t, 6H), 1.54 (q, 4H), 1.45–1.90 (m, 10H), 1.95 (t, 1H), 2.17 (m, 2H), 3.44 (m, 1H), 3.95 (m, 1H), 4.69 (m, 1H).

Preparation 7: Compound 8

Method: General Procedure 7.
Starting material VII: Compound 3.
Chromatography eluant: 15% to 25% ether in pet. ether.
NMR: $\delta$=0.05 (m, 12H), 0.81 (s, 3H), 0.86 (s, 9H), 0.89 (s, 9H), 0.83–0.90 (m, 6H), 1.46 (bs, 3H), 1.27–2.07 (m, 23H), 2.15 (bd, 1H), 2.31 (bd, 1H), 2.45 (bs, 2H), 2.55 (dd, 1H), 2.86 (m, 1H), 3.44 (m, 1H), 3.95 (m, 1H), 4.21 (m, 1H), 4.53 (m, 1H), 4.79 (m, 1H), 4.93 (m, 1H), 4.98 (m, 1H), 5.80 (d, 1H), 6.45 (d, 1H).

Preparation 8: Compound 9

Method: General Procedure 7.
Starting material VII: Compound 5.
Chromatography eluant: 5% ether in pet. ether.
NMR: $\delta$=0.05 (s, 9H), 0.06 (s, 9H), 0.80 (t, 6H), 0.81 (s, 3H), 0.85 (s, 9H), 0.86 (s, 9H), 0.89 (s, 9H), 1.46 (s, 3H), 1.25–2.10 (m, 19H), 2.10–2.25 (m, 3H), 2.33 (bd, 1H), 2.53 (dd, 1H), 2.86 (m, 1H), 4.22 (m, 1H), 4.52 (m, 1H), 4.93 (m, 1H), 4.98 (m, 1H), 5.82 (d, 1H), 6.45 (d, 1H).

Preparation 9: Compound 10

Method: General Procedure 7.
Starting material VII: Compound 7.
Chromatography eluant: 15% to 20% ether in pet. ether.
NMR: $\delta$=0.05 (m, 12H), 0.80 (bs, 3H), 0.82 (t, 6H), 0.86 (s, 9H), 0.88.(s, 9H), 1.45 (bs, 3H), 1.10–2.07 (m, 27H), 2.15 (m, 3H), 2.37 (bd, 1H), 2.48 (dd, 1H), 2.85 (bd, 1H), 3.44 (m, 1H), 3.93 (m, 1H), 4.20 (m, 1H), 4.50 (m, 1H), 4.70 (m, 1H), 4.91 (m, 1H), 4.98 (m, 1H), 5.81 (d, 1H), 6.44 (d, 1H).

Preparation 10: Compound 11

Method: General Procedure 8.
Starting material II: Compound 8.
Chromatography eluant: 15% to 20% ether in pet. ether.

NMR: δ=0.06 (m, 12H), 0.80 (s, 3H), 0.86 (s, 9H), 0.87 (s, 9H), 0.85–0.92 (m, 6H), 1.45 (bs, 3H), 1.25–2.05 (m, 23H), 2.07–2.27 (m, 2H), 2.43 (m 1H), 2.44 (s, 2H), 2.81 (m, 1H), 3.45 (m, 1H), 3.94 (m, 1H), 4.18 (m, 1H), 4.37 (m, 1H), 4.79 (m, 1H), 4.86 (m, 1H), 5.18 (m, 1H), 6.00 ( d, 1H ), 6.22 (d, 1H).

Preparation 11: Compound 12

Method: General Procedure 8.
Starting material II: Compound 10.
Chromatography eluant: 12,5% ether in pet. ether.
NMR: δ =0.06 (m, 12H), 0.79 (s, 3H), 0.81 (t, 6H), 0.86 (s, 9H), 0.87 (s, 9H), 1.45 (bs, 3H), 1.25–2.25 (m, 31H), 2.42 (dd, 1H), 2.81 (m, 1H), 3.43 (m, 1H), 3.93 (m, 1H), 4.17 (m, 1H), 4.38 (t, 1H), 4.70 (m, 1H), 4.86 (m, 1H), 5.19 (m, 1H), 6.00 (d, 1H), 6.21 (d, 1H).

Preparation 12: Compound 13 and 14

Method: General Procedure 9.
Starting material II: Compound 9.
Chromatography eluant: 1% to 10% ether in pet. ether or 10% dichloromethane in hexane.
NMR 13: δ=0.06 (m, 18H), 0.76 (s, 3H), 0.82 (t, 6H), 0.86 (s, 9H), 0.87 (s, 9H), 0.90 (s, 9H), 1.72 (bs, 3H), 1.20–1.87 (m, 13H), 1.92 (m, 1H), 2.16 (dd, 1H), 2.20–2.47 (m, 5H), 2.57 (dd, 1H), 2.75 (bd, 1H), 2.86 (m, 1H), 4.22 (m, 1H), 4.53 (m, 1H), 4.94 (m, 1H), 4.99 (m, 1H), 5.85 (d, 1H), 6.45 (d, 1H).
NMR 14: δ=0.06 (m, 18H), 0.75 (s, 3H), 0.83 (t, 6H), 0.85 (s, 9H), 0.86 (s, 9H), 0.90 (s, 9H), 1.84 (bs, 3H), 1.35–2.65 (m, 22H), 2.84 (bd, 1H), 4.22 (m, 1H), 4.52 (m, 1H), 4.94 (m, 1H), 4.98 (m, 1H), 5.87 (d, 1H), 6.43 (d, 1H).

Preparation 13: Compound 15

Method: General Procedure 9.
Starting material III: Compound 11.
Chromatography eluant: 33% ether in pet. ether (PLC).
NMR: δ=0.05 (m, 12H), 0.73 (s, 3H), 0.86 (s, 9H), 0.87 (s, 9H), 0.89 (t, 6H), 1.73 (bs, 3H), 2.47 (s, 2H), 1.35–2.55 (m, 18H), 2.69 (bd, 1H), 2.80 (m, 1H), 4.17 (m, 1H), 4.37 (m, 1H), 4.86 (m, 1H), 5.18 (m, 1H), 6.03 (d, 1H), 6.22 (d, 1H). cl Preparation 14: Compound 16
Method: General Procedure 8.
Starting material IV: Compound 13.
Chromatography eluant: 0% to 1% ether in pet. ether.
NMR: δ=0.06 (m, 18H), 0.75 (s, 3H), 0.83 (t, 6H), 0.86 (s, 9H), 0.86 (s, 9H), 0.87 (s, 9H), 1.72 (bs, 3H), 1.35–2.50 (m, 21H), 2.78 (m, 2H), 4.19 (m, 1H), 4.37 (m, 1H), 4.87 (m, 1H), 5.18 (m, 1H), 6.04 (d, 1H), 6.23 (d, 1a).

Preparation 15: Compound 17

Method: General Procedure 9.
Starting material III: Compound 12.
Chromatography eluant: 10% ether in pet. ether.
NMR: δ=0.06 (m, 12H), 0.74 (s, 3H), 0.86 (t, 6H), 0.86 (s, 9H), 0.87 (s, 9H), 1.45 (q, 4H), 1.72 (bs, 3H), 1.35–2.55 (m, 20H), 2.77 (m, 2H), 4.18 (m, 1H), 4.37 (m, H), 4.86 (m, 1H), 5.18 (m, 1H), 6.03 (d, 1H), 6.22 (d, 1H).

Preparation 16: Compound 18

Method: General Procedure 4.
Starting material VII: 3-Ethyl-1-pentin-3-ol.
Solvent: Dichloromethane (20 ml).
Base: N-ethyl-diisopropylamine (2.0 g)
Silylating agent: Chlorotrimethylsilane (1.7 g).
Reaction temperature: 20° C.
Reaction time: 1 hour.
Work-up: Additional extraction with phosphate buffer (pH 6.5, 0.07M, 60 ml).
NMR: δ=0.17 (s, 9H), 0.95 (t, 6H), 1.63 (q, 4H), 2.42 (s, 1H).

Preparation 17: Compound 19

Method: General Procedure 2.
Starting material VII: 2-Methyl-4-pentin-2-ol.
Chromatography eluant: 5% ether in pet. ether.
NMR: δ=1.34 (s, 3H), 1.35 (s, 3H), 1.51 (m, 4H), 1.67 (m, 1H), 1.84 (m, 1H), 2.00 (t, 1H), 2.44 (m, 2H), 3.45 (m, 1H), 3.97 (m, 1H), 4.81 (m, 1H).

Preparation 18: Compound 20

Method: General Procedure 3.
Starting material: Methyl magnesium iodide.
Purification by distillation in vacuo.
Bp. of compound 20: 58°–59° C./12 mmHg.
NMR: δ=1.24 (s, 6H), 1.69 (s, 1H), 1.75 (t, 2H), 1.98 (t, 1H), 2.31 (m, 2H).

Preparation 19: Compound 21

Method: General Procedure 2.
Starting material VII: Compound 20.
Chromatography eluant: 0% to 5% ether in pet. ether.
NMR: δ=1.21 (s, 3H), 1.23 (s, 3H), 1.51 (m, 4H), 1.64 (m, 1H), 1.78 (t, 2H), 1.83 (m, 1H), 1.92 (t, 1H), 2.29 (m, 2H), 3.45 (m, 1H), 3.93 (m, 1H), 4.73 (m, 1H).

Preparation 20: Compound 22

Method: General Procedure 8.
Starting material IV: Compound 14.
Chromatography eluant: 1% ether in pet. ether.
NMR: δ=0.05 (m, 18H), 0.74 (s, 3H), 0.83 (t, 6H), 0.86 (s, 18H), 0.87 (s, 9H), 1.84 (bs, 3H), 1.35–2.62 (m, 22H), 2.79 (bd, 1H), 4.18 (m, 1H), 4.37 (m, 1H), 4.87 (m, 1H), 5.18 (m, 1H), 6.05 (d, 1H), 6.21 (d, 1H).

Example 1

1(S),3(R)-Dihydroxy-20-(4-ethyl-4-hydroxy-1-hexyn-1-yl)-9,10-seco-pregna-5(Z), 7(E), 10(19), 17(20)(Z)-tetraene (Compound 101)
Method: General Procedure 10.
Starting material III: Compound 11.
Reaction temperature: 25° C.
Reaction time: 45 minutes.
Chromatography eluant: 50% to 0% pet. ether in ethyl acetate.

NMR: δ=0.76 (s, 3H), 0.90 (t, 6H), 1.75 (bs, 3H), 1.40–2.43 (m, 19H), 2.49 (bs, 2H), 2.60 (dd, 1H), 2.71 (m, 1H), 2.82 (m, 1H), 4.24 (m, 1H), 4.44 (m, 1H), 5.01 (m, 1H), 5.34 (m, 1H), 6.04 (d, 1H), 6.37 (d, 1H).

Example 2

1 (S), 3 (R)-Dihydroxy-20-(4-ethyl-4-hydroxy-1-hexyn-1-yl)-9, 10-seco-pregna-5(Z), 7(E), 10(19), 17(20)(Z)-tetraene (Compound 101)

Method: General Procedure 11.

Starting material V: Compound 15.

Reaction temperature: 60° C.

Reaction time: 1 hour.

Chromatography eluant: 50% to 0% pet. ether in ethyl acetate.

NMR: δ=0.76 (s, 3H), 0.90 (t, 6H), 1.75 (bs, 3H), 1.40–2.43 8m, 19H), 2.49 (bs, 2H), 2.60 (d, 1H), 2.71 (m, 1H), 2.82 (m, 1H), 4.24 8m, 1H), 4.44 (m, 1H), 5.01 (m, 1H ), 5.34 (m, 1H), 6.04 (d, 1H), 6.37 (d, 1H).

Example 3

1(S), 3(R)-Dihydroxy-20-(5-ethyl- 5-hydroxy-1-heptyn-1-yl)-9,10-seco-pregna-5(Z), 7(E), 10(19), 17(20)(Z)-tetraene (Compound 102)

Method: General Procedure 10.

Starting material V: Compound 16.

Reaction temperature: 50° C.

Reaction time: 10 minutes.

Chromatography eluant: 50% to 33% pet. ether in ethyl acetate.

NMR: δ=0.75 (s, 3H), 0.87 (t, 6H), 1.72 (bs, 3H), 1.35–2.50 (m, 23H), 2.61 (dd, 1H), 2.67–2.90 (m, 2H), 4.24 (m, 1H), 4.44 (m, 1H), 5.01 (m, 1H), 5.34 (m, 1H), 6.04 (d, 1H), 6.38 (d, 1H).

Example 4

1(S), 3(R)-Dihydroxy-20-(5-ethyl-5-hydroxy-1-heptyn-1-yl)-9,10-seco-pregna-5(Z), 7(E), 10(19), 17(20) (Z)-tetraene (Compound 102)

Method: General Procedure 11.

Starting material V: Compound 16.

Reaction temperature: 100° C.

Reaction time: 17 hours.

Chromatography eluant: 40% pet. ether in ethyl acetate.

NMR: δ=0.75 (s, 3H), 0.87 (t, 6H), 1.72 (bs, 3H), 1.35–2.50 (m, 23H), 2.61 (dd, 1H), 2.67–2.90 (m, 2H), 4.24 (m, 1H), 4.44 (m, 1B), 5.01 (m, 1H), 5.34 (m, 1H), 6.04 (d, 1H), 6.38 (d, 1H).

Example 5

1(S),3(R)-Dihydroxy-20-(6-ethyl-6-hydroxy-1-octyn-1-yl)-9,10-seco-pregna-5(Z), 7(E), 10(19), 17(20) (Z)-tetraene (Compound 103)

Method: General Procedure 11.

Starting material V: Compound 17.

Reaction temperature: 60° C.

Reaction time: 90 minutes.

Chromatography eluant: 50% to 0% pet. ether in ethyl acetate.

NMR: δ=0.76 (s, 3H), 0.87 (t, 6H), 1.47 (q, 4H), 1.73 (bs, 3H), 1.40–2.50 (m, 21H), 2.60 (dd, 1H), 2.78 (m, 2H), 4.24 (m, 1H), 4.44 (m, 1H), 5.01 (m, 1H), 5.34 (m, 1H), 6.04 (d, 1H), 6.38 (d, 1H).

Example 6

1(S), 3(R)-Dihydroxy-20-(5-ethyl-5-hydroxy-1-heptyn-1-yl)-9, 10-seco-pregna-5(Z), 7(E), 10(19), 17(20)(E)-tetraene (Compound 112)

Method: General Procedure 11.

Starting material V: Compound 22.

Reaction temperature: 100° C.

Reaction time: 20 hours.

Chromatography eluant: 50% to 0% pet. ether in ethyl acetate.

NMR: δ=0.74 (s, 3H), 0.86 (t, 6H), 1.49 (q, 4H), 1.83 (bs, 3H), 2.41 (t, 2H), 1.15–2.65 (m, 19H), 2.79 (m, 1H), 4.22 (m, 1H), 4.43 (m, 1H), 5.00 (m, 1H), 5.33 (m, 1H), 6.04 (d, 1H), 6.35 (m, 1H).

Example 7

Capsules Containing Compound 102

Compound 102 was dissolved in arachis oil to a final concentration of 1 μg of Compound 102/ml oil. 10 Parts by weight of gelatine, 5 parts by weight glycerine, 0.08 parts by weight potassium sorbate, and 14 parts by weight distilled water were mixed together with heating and formed into soft gelatine capsules. These were then filled each with 100 μl of Compound 102 in oil solution, such that each capsule contained 0.1 μg of Compound 102.

Example 8

Dermatological Cream Containing Compound 102

In 1 g almond oil was dissolved 0.05 mg of Compound 102. To this solution was added 40 g of mineral oil and 20 g of self-emulsifying beeswax. The mixture was heated to liquify. After the addition of 40 ml hot water, the mixture was mixed well. The resulting cream contains approximately 0.5 μg of Compound 102 per gram of cream.

What we claim is:

1. A compound of the formula I

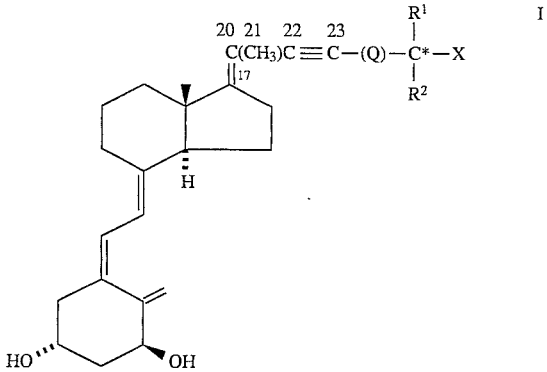

wherein X is hydrogen or hydroxy; $R^1$ and $R^2$ which may be the same or different, stand for hydrogen or a $C_1$–$C_6$ hydrocarbyl radical optionally substituted with one or more deuterium or fluorine atoms; or $R^1$ and $R^2$, taken together with the carbon atom (starred in formula I) bearing the group X, can form a $C_3$–$C_8$ carbocyclic ring; Q is a single bond or a $C_1$–$C_8$ hydrocarbylene diradical optionally substituted with one or more deuterium or fluorine atoms; or a prodrug of I in which one or more of the hydroxy groups are masked as groups which can be reconverted to hydroxy groups in vivo.

2. A compound of formula I of claim 1 in which X is hydroxy.

3. A compound of claim 2 in which Q is —$(CH_2)_n$—, where n is an integer from 0 to 3.

4. A diastereoisomer of a compound according to any one of claims 1–3, in pure form.

5. A compound according to claim 1 which is
   a) 1(S), 3(R)-Dihydroxy-20-(4-ethyl-4-hydroxy-1-hexyn-1-yl)-9,10-seco-pregna-5(Z), 7(E), 10(19), 17(20)(Z)-tetraene
   b) 1(S), 3(R)-Dihydroxy-20-(5-ethyl-5-hydroxy-1-heptyn-1yl)-9,10-seco-pregna-5(Z), 7(E), 10(19), 17(20)(Z)-tetraene or
   c) 1(S), 3(R)-Dihydroxy-20-(6-ethyl-6-hydroxy-1-octyn-1-yl)-9,10-seco-pregna-5(Z), 7(E), 10(19), 17(20)(Z)-tetraene.

6. A pharmaceutical composition containing an effective amount of one or more of the compounds of claim 1, and a pharmaceutically acceptable, non-toxic carrier.

7. A pharmaceutical composition according to claim 6 in dosage unit form containing from 0.1 ppm to 0.1% by weight of the dosage unit of a compound of formula I.

8. A method for producing a compound of formula I:

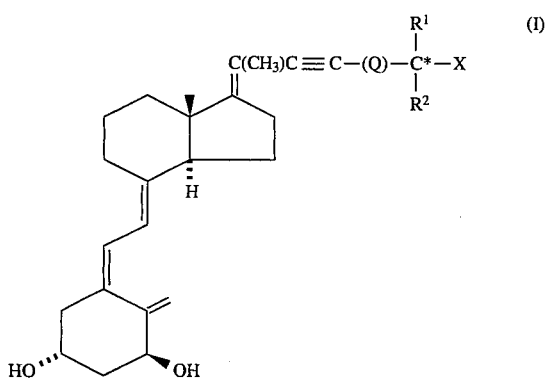

wherein X is hydrogen or hydroxy; $R^1$ and $R^2$, which may be the same or different, stand for hydrogen or a $C_1$–$C_6$ hydrocarbyl radical, optionally substituted with one or more deuterium or fluorine atoms; or $R^1$ and $R^2$, taken together with the carbon atom (starred in formula I) bearing the group X, can form a $C_3$–$C_8$ carbocyclic ring; Q is a single bond or a $C_1$–$C_8$ hydrocarbylene diradical, optionally substituted with one or more deuterium or fluorine atoms, comprising
   a) reacting a 1(S), 3(R)-bis-(hydroxy-protected)-9,10-seco-pregna-5(E), 7(E), 10(19)-trien-20-one with a suitable base and the anion $R^-$ derived from an acetylenic compound RH, in which R is

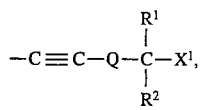

where $R^1$, $R^2$, and Q have the above meanings and $X^1$ stands for hydrogen, hydroxy, or a protected hydroxy group, to form a product of formula II

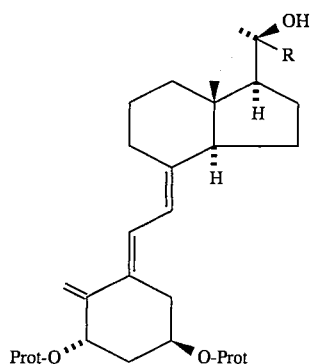

in which R has the above meaning and O-Prot is a protected hydroxy group;
   b) subjecting the compound of formula II to a triplet-sensitized photoisomerization to form a compound of formula III

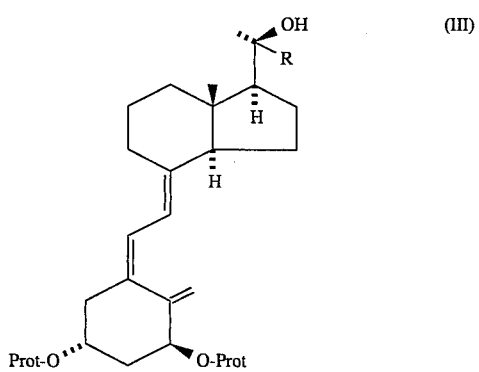

in which R and O-Prot have the above meanings;
   c) dehydrogenating the compound of formula III by acid catalyzed dehydrogenation to form a compound of formula V

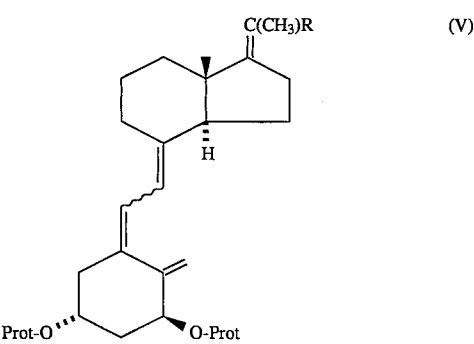

in which R and O-Prot have the above meanings; and
   d) deprotecting the compound of formula V to form the desired compound of formula I.

9. A method according to claim 8 in which steps b) and c) are performed in the reverse order.

10. A method according to claim 8 in which steps c) and d) are performed in one combined procedure. of the dosage unit of a compound of formula I.

11. The method according to claim 10 wherein steps c) and d) are performed by means of hydrofluoric acid.

12. The method of claim 8 wherein the sidechain R is optionally subjected to functional group modification in any one of steps b), c) or d).

13. The method of claim 8 wherein the isomers of formula V produced in step c) are separated.

14. The method of claim 8 wherein the compound of formula V is deprotected with hydrofluoric acid or tetra-(n-butyl)ammonium fluoride.

15. The method of claim 8 where the compound of formula I produced in step d) is further modified to form a prodrug by masking the hydroxy groups into groups which can be reconverted to hydroxy groups in vivo.

* * * * *

UNITED STATES PATENT AND TRADEMARK OFFICE
CERTIFICATE OF CORRECTION

PATENT NO. : 5,545,633
DATED : August 13, 1996
INVENTOR(S) : BRETTING

It is certified that error appears in the above-indentified patent and that said Letters Patent is hereby corrected as shown below:

Column 9, under the first reaction, below "VIII" (both occurrences) change "$X^1 = CR^3$ to $X^1 = OR^3$.

Column 11,  line 49, change "RH=H — C≡C-" to RH= H-C≡C-.

Column 18,  line 20, change "multipier" to --multiplet--;
line 60, change "Scheme" to --Scheme--.

Column 19,  lines 20 and 21, should be made footnote 1 at the end of column 19.

Column 20,  line 29, delete "31" and insert a minus sign -- - --.

Column 23,  line 47, delete "cl";
same line, "Preparation 14: Compound 16" should be a separate heading immediately following line 47.
line 56, change "(d,1a)" to --(d,1H)--;
line 66, change "(m,H)" to --(m,1H)--.

Column 25,  line 53, change "(m,1B)" to --(m,1H)--.

Column 27,  line 19, change "tyn-1yl)" to --tyn-1-yl)--.

UNITED STATES PATENT AND TRADEMARK OFFICE
CERTIFICATE OF CORRECTION

PATENT NO. : 5,545,633

DATED : August 13, 1996

INVENTOR(S) : BRETTING

It is certified that error appears in the above-indentified patent and that said Letters Patent is hereby corrected as shown below:

Column 28, lines 59-60, delete "of the dosage unit of a compound of formula 1".

Signed and Sealed this

Seventeenth Day of June, 1997

Attest:

Attesting Officer

BRUCE LEHMAN

Commissioner of Patents and Trademarks